(12) United States Patent  
Kaplan et al.

(10) Patent No.: US 6,488,689 B1
(45) Date of Patent: *Dec. 3, 2002

(54) METHODS AND APPARATUS FOR TRANSPERICARDIAL LEFT ATRIAL APPENDAGE CLOSURE

(75) Inventors: Aaron V. Kaplan, 851 Carnation Ct., Los Altos, CA (US) 94024; Jordan T. Bajor, Palo Alto, CA (US)

(73) Assignee: Aaron V. Kaplan, Los Altos, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/315,601

(22) Filed: May 20, 1999

(51) Int. Cl.[7] ................................. A61B 17/10
(52) U.S. Cl. ......................................... 606/139
(58) Field of Search ................. 606/139, 194; 604/49, 175, 96; 128/898

(56) References Cited

U.S. PATENT DOCUMENTS

| | | |
|---|---|---|
| 3,496,932 A | 2/1970 | Prisk et al. |
| 4,030,509 A | 6/1977 | Heilman et al. |
| 4,257,278 A | 3/1981 | Papadofrangakis et al. |
| 4,319,562 A | 3/1982 | Crosby |
| 4,662,377 A | 5/1987 | Heilman et al. |
| 4,765,341 A | 8/1988 | Mower et al. |
| 4,817,608 A | 4/1989 | Shapland et al. |
| 4,944,753 A | 7/1990 | Burgess et al. |
| 4,991,578 A | 2/1991 | Cohen et al. |
| 4,991,603 A | 2/1991 | Cohen et al. |
| 4,998,975 A | 3/1991 | Cohen et al. |
| 5,033,477 A | 7/1991 | Chin et al. |
| 5,181,123 A | 1/1993 | Swank |
| 5,243,977 A | 9/1993 | Trabucco et al. |
| 5,269,326 A | 12/1993 | Verrier |
| 5,306,234 A * | 4/1994 | Johnson ................ 604/49 |
| 5,336,252 A | 8/1994 | Cohen |
| 5,385,156 A | 1/1995 | Oliva |
| 5,423,821 A | 6/1995 | Pasque |
| 5,433,730 A | 7/1995 | Alt |
| 5,498,228 A | 3/1996 | Royalty et al. |
| 5,582,580 A | 12/1996 | Buckman, Jr et al. |
| 5,634,895 A | 6/1997 | Igo et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |

(List continued on next page.)

FOREIGN PATENT DOCUMENTS

WO    WO 98/05289    2/1998

*Primary Examiner*—Henry J. Recla
*Assistant Examiner*—Tan-Uyen T. Ho
(74) *Attorney, Agent, or Firm*—Cook, Alex, McFarron, Manzo, Cummings & Mehler, Ltd.

(57) ABSTRACT

Methods and apparatus for closing a left atrial appendage are described. The methods rely on introducing a closure tool from a location beneath the rib cage, over an epicardial surface, and to the exterior of the left atrial appendage. The closure device may then be used to close the left atrial appendage, preferably at its base, by any one of a variety of techniques. A specific technique using graspers and a closing loop is illustrated.

39 Claims, 13 Drawing Sheets

U.S. PATENT DOCUMENTS

| | | | |
|---|---|---|---|
| 5,681,278 | A | 10/1997 | Igo et al. |
| 5,682,906 | A | 11/1997 | Sterman et al. |
| 5,683,445 | A | 11/1997 | Swoyer |
| 5,693,091 | A | 12/1997 | Larson, Jr. et al. |
| 5,702,430 | A | 12/1997 | Larson, Jr. et al. |
| 5,707,336 | A | 1/1998 | Rubin |
| 5,716,392 | A | 2/1998 | Bourgeois et al. |
| 5,728,151 | A | 3/1998 | Garrison et al. |
| 5,752,526 | A | 5/1998 | Cosgrove |
| 5,797,870 | A | 8/1998 | March et al. |
| 5,797,946 | A | 8/1998 | Chin |
| 5,799,661 | A | 9/1998 | Boyd et al. |
| 5,823,946 | A | 10/1998 | Chin |
| 5,827,216 | A | 10/1998 | Igo et al. |
| 5,840,059 | A | 11/1998 | March et al. |
| 5,865,791 | A | 2/1999 | Whayne et al. |
| 5,871,531 | A | 2/1999 | Struble |
| 5,879,375 | A | 3/1999 | Larson, Jr. et al. |
| 5,882,299 | A | 3/1999 | Rastegar et al. |
| 5,895,298 | A | 4/1999 | Faupel et al. |
| 5,897,586 | A | 4/1999 | Molina |
| 5,900,433 | A | 5/1999 | Igo et al. |
| 5,910,124 | A | 6/1999 | Rubin |
| RE36,269 | E | 8/1999 | Wright |
| 5,941,819 | A | 8/1999 | Chin |
| 5,961,440 | A | 10/1999 | Schweich, Jr. et al. |
| 5,964,699 | A | 10/1999 | Rullo et al. |
| 5,968,010 | A | 10/1999 | Waxman et al. |
| 5,984,866 | A | 11/1999 | Rullo et al. |
| 5,991,668 | A | 11/1999 | Leinders et al. |
| 5,997,525 | A | 12/1999 | March et al. |
| 6,006,122 | A | 12/1999 | Smits |
| 6,015,382 | A | 1/2000 | Zwart et al. |
| 6,059,750 | A | 5/2000 | Fogarty et al. |
| 6,081,738 | A | 6/2000 | Hinohara et al. |
| 6,083,153 | A | 7/2000 | Rullo et al. |
| 6,090,042 | A | 7/2000 | Rullo et al. |
| 6,095,968 | A | 8/2000 | Snyders |
| 6,110,170 | A | 8/2000 | Taylor et al. |
| 6,120,431 | A | 9/2000 | Magovern et al. |
| 6,148,230 | A | 11/2000 | KenKnight |
| 6,149,595 | A | 11/2000 | Seitz et al. |
| 6,155,968 | A | 12/2000 | Wilk |
| 6,157,852 | A | 12/2000 | Selmon et al. |
| 6,162,195 | A | 12/2000 | Igo et al. |
| 6,167,889 | B1 | 1/2001 | Benetti |
| 6,199,556 | B1 | 3/2001 | Benetti et al. |
| 6,200,303 | B1 | 3/2001 | Verrior et al. |
| 6,206,004 | B1 | 3/2001 | Schmidt et al. |
| 6,224,584 | B1 | 5/2001 | March et al. |
| 6,237,605 | B1 | 5/2001 | Vaska et al. |
| 6,241,667 | B1 | 6/2001 | Vetter et al. |
| 6,258,021 | B1 | 7/2001 | Wilk |
| 6,266,550 | B1 | 7/2001 | Selmon et al. |
| 6,283,127 | B1 | 9/2001 | Sterman et al. |
| 6,293,906 | B1 | 9/2001 | Hoek et al. |
| 6,296,630 | B1 | 10/2001 | Altman et al. |
| 6,311,692 | B1 | 11/2001 | Vaska et al. |
| 6,311,693 | B1 | 11/2001 | Sterman et al. |
| 6,314,962 | B1 | 11/2001 | Vaska et al. |
| 6,314,963 | B1 | 11/2001 | Vaska et al. |
| 6,319,201 | B1 | 11/2001 | Wilk |
| 6,333,347 | B1 | 12/2001 | Hunter et al. |

\* cited by examiner

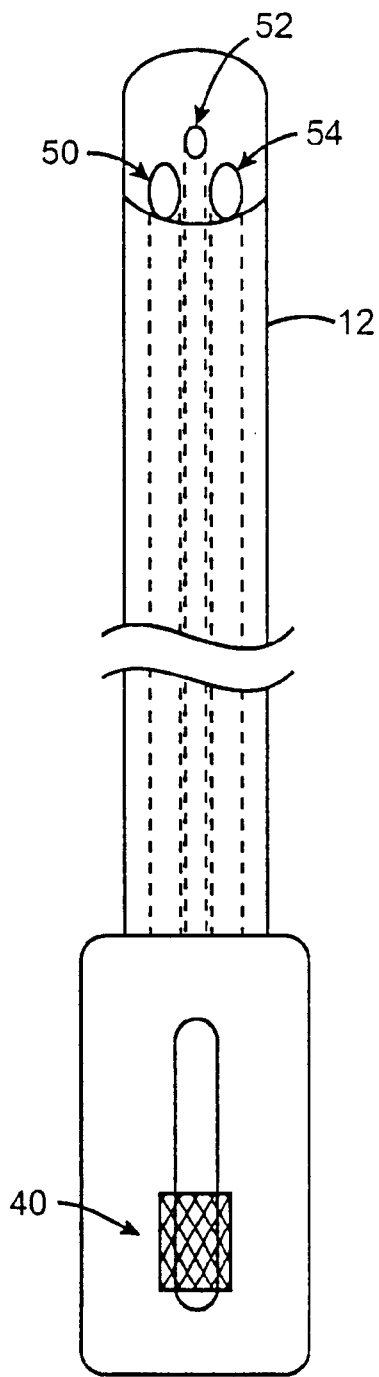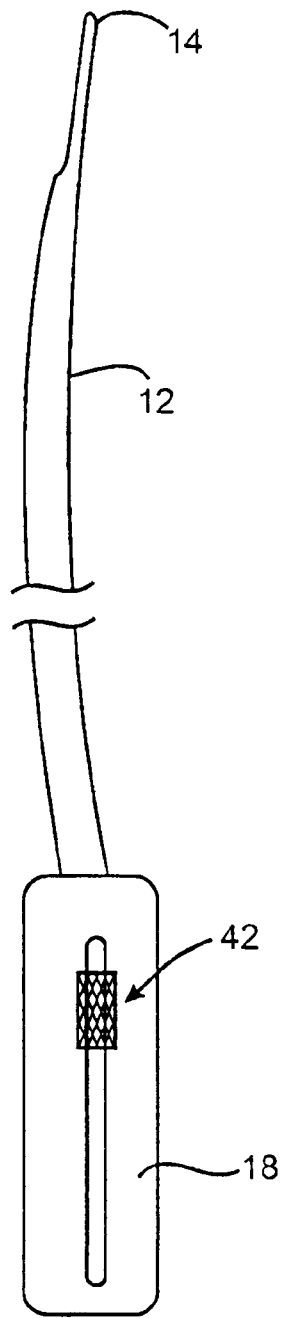
FIG. 4C
FIG. 4A
FIG. 4B

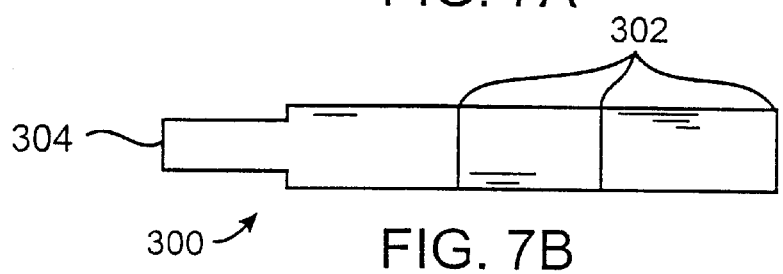
FIG. 7C  FIG. 7A
FIG. 7B
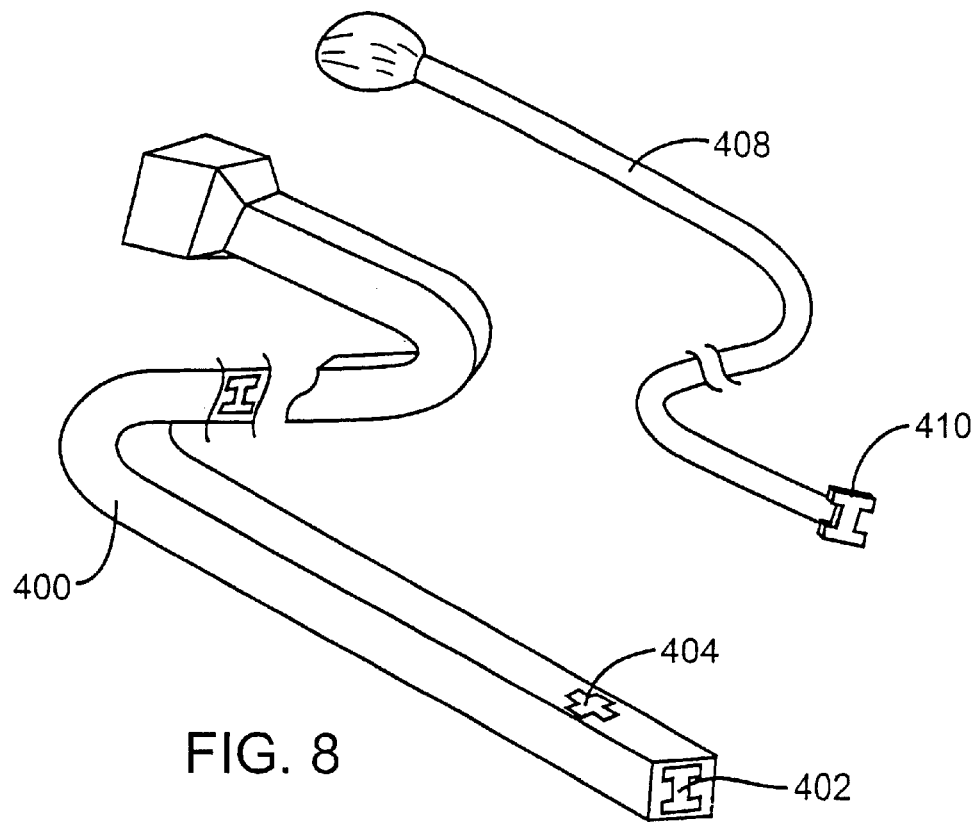
FIG. 8

METHODS AND APPARATUS FOR TRANSPERICARDIAL LEFT ATRIAL APPENDAGE CLOSURE

BACKGROUND OF THE INVENTION

1. Field of the Invention

The present invention relates generally to medical methods and apparatus. More particularly, the present invention relates to a method and device for the minimally invasive closure of a left atrial appendage of the heart.

Atrial fibrillation is a common cardiac rhythm disorder affecting a population of approximately 2.5 million patients in the United States alone. Atrial fibrillation results from a number of different causes and is characterized by a rapid chaotic heart beat. In addition to the risks associated with a disordered heart beat, patients with atrial fibrillation also have an increased risk of stroke. It has been estimated that approximately 75,000 atrial fibrillation patients each year suffer a stroke related to that condition. It appears that strokes in these patients result from emboli many of which may originate from the left atrial appendage. The irregular heart beat causes blood to pool in the left atrial appendage, allowing clots to accumulate over time. From time to time, clot may dislodge from the left atrial appendage and may enter the cranial circulation causing a stroke, the coronary circulation causing a myocardial infarction, the peripheral circulation causing limb ischemia, as well as other vascular beds.

Significant efforts have been made to reduce the risk of stroke in patients suffering from atrial fibrillation. Most commonly, those patients are treated with blood thinning agents, such as coumadin, to reduce the risk of clot formation. While such treatment can significantly reduce the risk of stroke, it also increases the risk of bleeding and for that reason is inappropriate for many atrial fibrillation patients.

As an alternative to drug therapy, surgical procedures for closing the left atrial appendage have been proposed. Most commonly, the left atrial appendage has been closed or removed in open surgical procedures, typically where the heart has stopped and the chest opened through the sternum. Because of the significant risk and trauma of such procedures, left atrial appendage removal occurs almost exclusively when the patient's chest is opened for other procedures, such as coronary artery bypass or valve surgery.

For that reason, alternative procedures which do not require opening of the patient's chest, i.e., a large median sternotomy, have been proposed. U.S. Pat. No. 5,306,234 to Johnson describes a thoracoscopic procedure where access to the pericardial space over the heart is achieved using a pair of intercostal penetrations (i.e., penetrations between the patients ribs) to establish both visual and surgical access. While such procedures may be performed while the heart remains beating, they still require deflation of the patient's lung and that the patient be placed under full anesthesia. Furthermore, placement of a chest tube is typically required to reinflate the lung, often requiring a hospitalization for a couple of days.

U.S. Pat. No. 5,865,791, to Whayne et al. describes a transvascular approach for closing the left atrial appendage. Access is gained via the venous system, typically through a femoral vein, a right internal jugular vein, or a subclavian vein, where a catheter is advanced in an antegrade direction to the right atrium. The intra-atrial septum is then penetrated, and the catheter passed into the left atrium. The catheter is then positioned in the vicinity of the left atrial appendage which is then fused closed, e.g., using radiofrequency energy, other electrical energy, thermal energy, surgical adhesives, or the like. Whayne et al. further describes a thoracoscopic procedure where the pericardium is penetrated through the rib cage and a lasso placed to tie off the neck of the left atrial appendage. Other fixation means described include sutures, staples, shape memory wires, biocompatible adhesives, tissue ablation, and the like. The transvascular approach suggested by Whayne et al. is advantageous in that it avoids the need to penetrate the patient's chest but suffers from the need to penetrate the intra-atrial septum, may not provide definitive closure, requires entry into the left atrial appendage which may dislodge clot and requires injury to the endocardial surface which may promote thrombus formation. A thoracoscopic approach which is also suggested by Whayne et al. suffers from the same problems as the thoracoscopic approach suggested by Johnson.

For all these reasons, it would be desirable to provide improved and alternative methods and procedures for performing minimally invasive closure of the left atrial appendage. Such methods and procedures will preferably be capable of being performed on patients who have received only a local anesthetic and whose hearts have not been stopped. It would be further desirable to provide methods and procedures which approach the left atrial appendage without the need to perform a thoracotomy (penetration through the intracostal space) or the need to perform a transeptal penetration and/or perform the procedure within the left atrium or left atrial appendage. More specifically, it would be preferable to provide methods and procedures which permitted access to the pericardial space from the xiphoid region of a patient's chest. In addition to the improved and alternative methods and procedures, it would be desirable to provide specialized instruments, devices, and systems for accessing a region over a patient's left atrial appendage from a sub-xiphoid access point to permit closure of the left atrial appendage.

At least some of these objectives will be met by the inventions described herein below.

2. Description of the Background Art

U.S. Pat. Nos. 5,306,234 and 5,865,791 have been described above. U.S. Pat. No. 3,496,932 and PCT publication WO 98/05289 describe methods and apparatus which employ a sub-xiphoid approach for direct cardiac massage.

SUMMARY OF THE INVENTION

The present invention provides alternative and improved methods and apparatus for closing a left atrial appendage of a patient, particularly a patient at risk of occlusive stroke resulting from emboli released from the left atrial appendage. The most likely patient population for the procedures will be patients suffering from atrial fibrillation which can result in clot and thrombus generation in the left atrial appendage, as described above. The methods and apparatus of the present invention permit procedures to be performed on a conscious sedated patient, often in an ambulatory surgical setting where the patient may be released shortly after the procedure is completed. In particular, the methods and apparatus of the present invention eliminates the need for a large incision and division of the sternum, i.e., median sternotomy. The present invention further eliminates the need to take down (deflate) a lung to access a left atrial appendage, as is usually required in thoracoscopic procedures performed via intracostal access.

The methods of the present invention will be performed in a minimally invasive manner, i.e., where access to the pericardial space overlying the patient's left atrial appendage is accomplished through percutaneous penetrations through the patient's skin. Rather than passing through the rib cage, as with prior thoracoscopic techniques, the present invention relies on a "sub-xiphoid" approach where the percutaneous penetration is first made beneath the rib cage, preferably between the xiphoid and adjacent costal cartilage, and an atrial appendage closure tool advanced through the penetration, over the epicardial surface (in the pericardial space) to reach a location adjacent to the exterior of the left atrial appendage. The closure tool can then be used to close the left atrial appendage to prevent the formation of clot and the release of emboli from the atrium.

Closure can be effected in a variety of ways. It is presently preferred to position a loop of material, such as suture, wire, mesh, tape, or the like, over the appendage and cinch the loop tighter to close the interior of the appendage. A variety of alternative closure techniques would also find use, including suturing (using remotely actuated suturing instruments), stapling, clipping, fusing, gluing, clamping, riveting, or the like. Such closure will generally be intended to be permanent, i.e., it will remain indefinitely after the closure tool is removed, but in some instances could be reversible, i.e., the left atrial appendage could be reopened on a subsequent procedure.

Thus, a method according to the present invention for closing a left atrial appendage of a patient's heart comprises positioning a closure instrument through a percutaneous passage beneath the rib cage, over an epicardial surface, and adjacent to the left atrial appendage. The left atrial appendage is then closed, usually using one of the techniques described above. The positioning step may comprise making an incision usually between a costal cartilage and a xiphoid of the patient, establishing a tract beneath the rib cage. Alternatively the incision may be made superficial to the xiphoid or sternum after which a tract is made through the rib cage to the pericardial space, and will preferably include placing an access sheath through the incision into the pericardial space. The incision may be made using a scalpel or other conventional surgical tool, but could also be made using a trocar and cannula assembly, such as those used in laparoscopic surgery, where the trocar could then be removed leaving the cannula in place as the sheath of the present invention. Use of a trocar and cannula may be less preferred, however, since there is an increased risk of injuring the heart if the trocar and cannula assembly is introduced in a blind fashion.

A closure instrument is then introduced through the sheath into the pericardial space, and over an epicardial surface to the exterior of the left atrial appendage, as described above. Preferably, a distal end of the tool will be introduced into an atrioventricular groove which lies just beneath the atrial appendage.

Preferably, once the closure tool has been introduced, advancement and positioning can be performed under conventional imaging techniques, such as fluoroscopic imaging. Often, the closure tool will include or be compatible with imaging scopes which may be introduced through the tool. The use of imaging scopes will be particularly useful during the closure procedure where the left atrial appendage is manipulated as described in more detail below. In such instances, it will frequently be desirable to introduce a saline or other clear fluid into the pericardial space to facilitate viewing.

Once the closure tool is properly positioned, closure may be effected by any of the techniques described above, including looping, suturing, stapling, clipping, fusing, clamping, riveting, or the like. Preferably, the closure will be directed at the base region of the left atrial appendage. Optionally, closing the appendage may further comprise grasping the exterior of the left atrial appendage prior to the actual closing step. Grasping will typically be performed with the conventional grasping tool. As described below, a preferred closure technique is to first grasp the exterior of the left atrial appendage with a grasping tool and subsequently advance a closure loop over the tool on to the exterior of the appendage. A closure loop may then be cinched or otherwise closed or allowed to close, and the tools removed.

A variety of specific instruments, devices, and systems may be devised for performing the methods of the present invention. An exemplary device for closing a left atrial appendage according to the methods of the present invention is described in detail in the descriptions that follow. The device comprises a shaft having a proximal end and a distal end, where the distal end is adapted to percutaneously enter the pericardial space, be advanced over an epicardial surface, and then approach the exterior of the left atrial appendage. Preferably, the shaft has a length in the range from 10 cm to 40 cm, a width in the range from 2 mm to 20 mm, and a thickness in the range from 1 mm to 10 mm. Usually, the shaft will be curved over its length to be compatible with the curvature of the heart. The shaft may include a means to alter the curvature to accommodate variations in anatomy. Similarly, the device may preferably include a crescent-shaped cross-section to also conform to the shape of the exterior of the heart. The device will carry a mechanism or means for closing the left atrial appendage when the distal end of the shaft is positioned adjacent to the appendage. Usually, the closure mechanism will be introducable through one or more lumens formed in the shaft. In a particularly preferred configuration, the distal end of the shaft will be configured to lie within the atrioventricular groove of the heart, and at least one lumen through the shaft will have an exit port spaced inwardly from the distal end of the shaft by a distance in the range from 0.5 cm to 5 cm. In this way, the port will be positioned properly to access the free end of the atrial appendage for performing the closing procedures. In addition, the shaft may have one or more additional lumens (for a total of two, three, or more lumens through the shaft) in order to provide additional capabilities, including introduction and use of a viewing scope, infusion and perfusion of fluids, particularly the infusion of saline to facilitate viewing. Optionally, the lumens can be used to introduce an anesthetic agent, such as lidocaine, in order to reduce pain or to introduce an anti-arrhythmic agent to reduce myocardial irritability.

The present invention still further comprises kits including the closure devices just described. The kits will further include instructions for use according to the methods described above, and optionally further include packaging for holding all components of the kit together. Additionally, the kits may include the access sheath which is placed through the percutaneous penetration tracks as the pericardial space. The access sheath may be in the form of a trocar and cannula assembly, although this will usually not be preferred.

BRIEF DESCRIPTION OF THE DRAWINGS

FIGS. 4A–4C are orthogonal views of the closure device of FIG. 3.

FIGS. 7A–7C illustrate an exemplary clip which may be used in performing the closure methods of the present invention.

FIG. 8 illustrates a clip insertion tool useful for placing the clip of FIGS. 7A–7C according to the methods of the present invention.

DESCRIPTION OF THE SPECIFIC EMBODIMENTS

Figure 1:
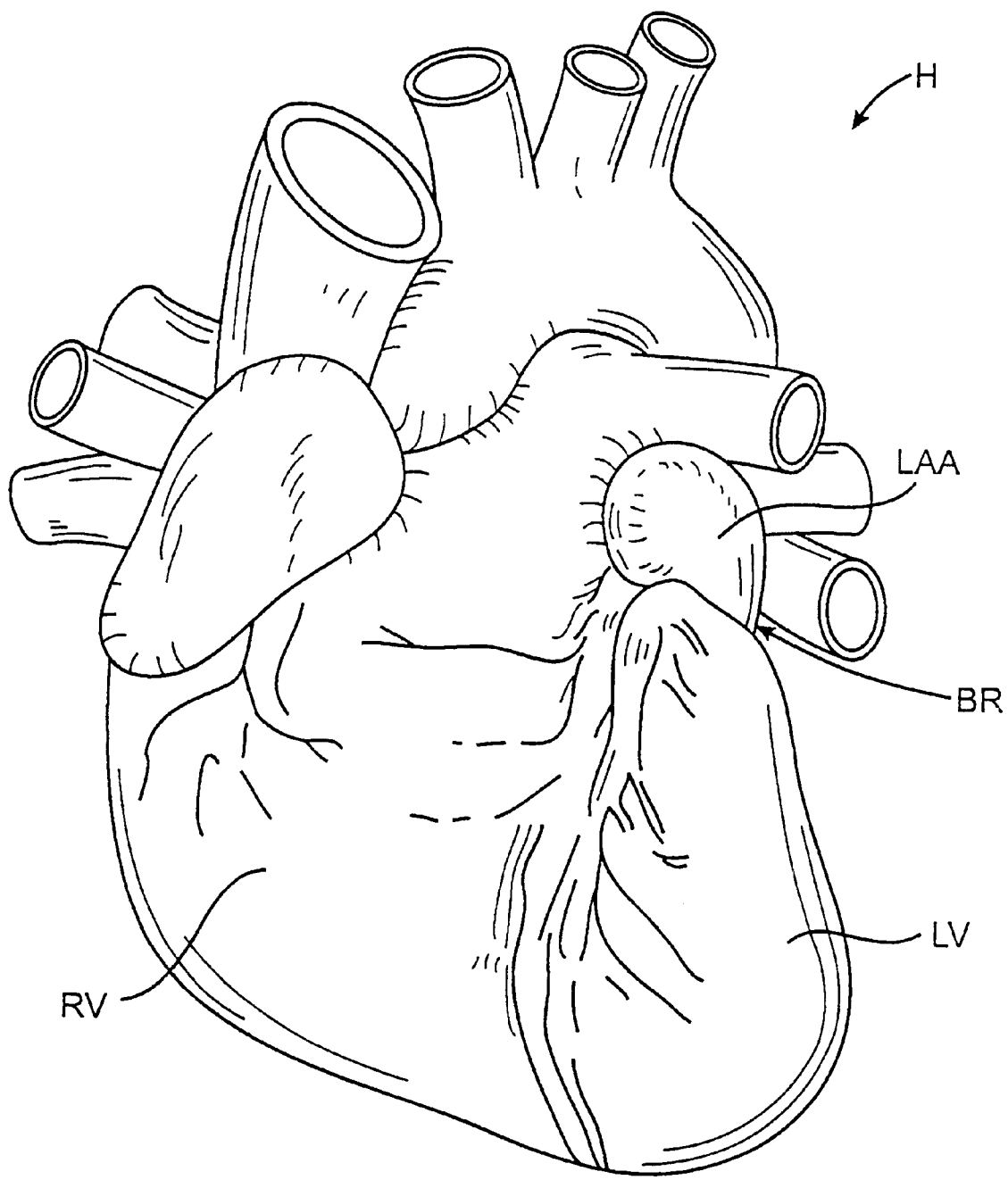
FIG. 1 is an anterior view of a heart illustrating the position of the left atrial appendage relative to the remaining structures of the heart.

FIG. 1 is an anterior view of a heart illustrating the right ventricle RV, the left ventricle LV, and the left atrial appendage LAA. The methods and apparatus of the present invention are intended to place a closure structure over or otherwise close off the base region BR of the left atrial appendage. By closing off the base region BR, the exchange of materials between the left atrial appendage LAA and the left atrium LA will be stopped. Thus, the release of emboli from the left atrial appendage into the left atrium will be stopped.

Figure 2:
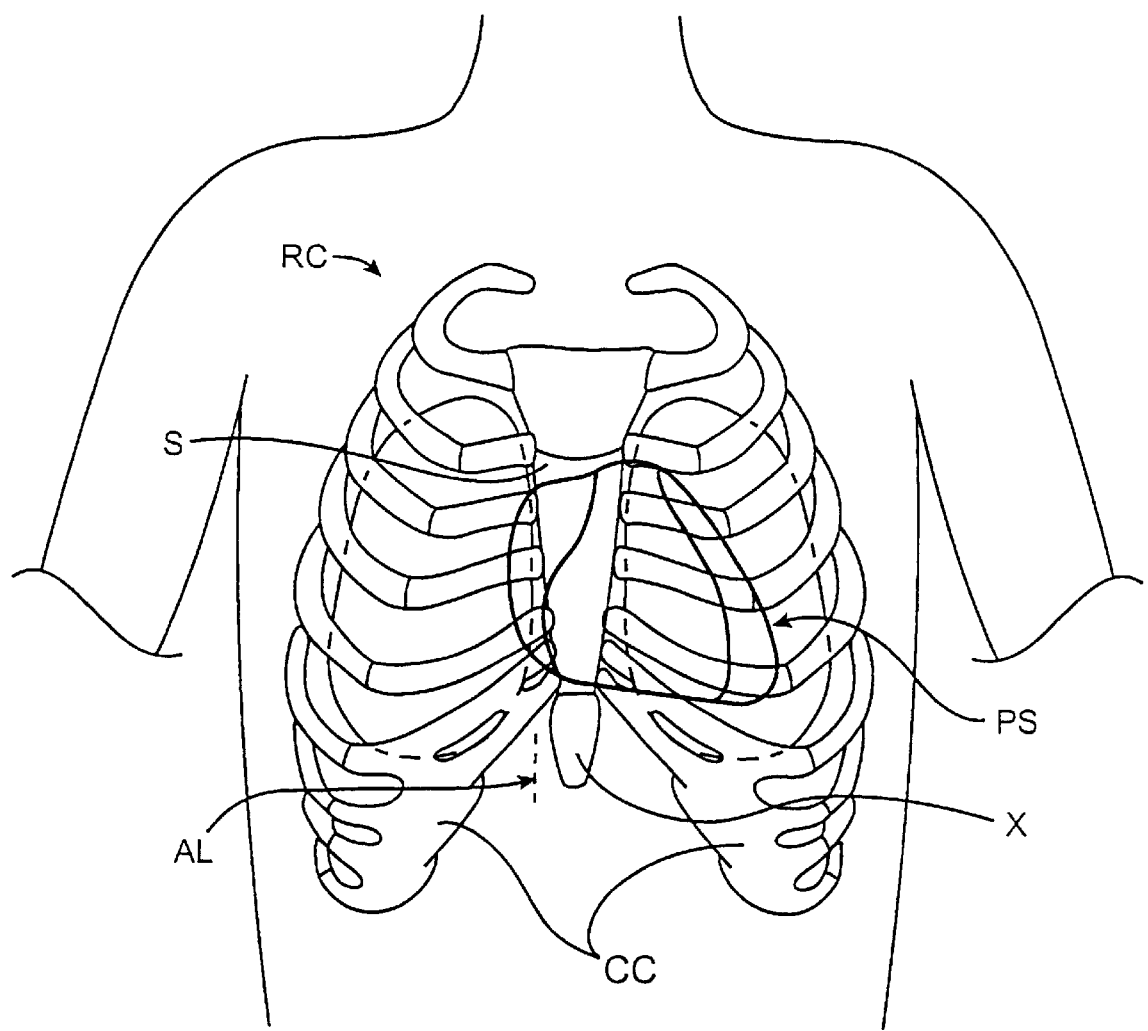
FIG. 2 shows the position of the heart in an associated chest cavity and illustrates a preferred percutaneous access site for performing the methods of the present invention.

Referring now to FIG. 2, the heart is located within the pericardial space PS located beneath the patient's rib cage RC. The sternum S is located in the center of the rib cage RC and terminates at its lower end in the xiphoid X. On either side of the xiphoid are the costal cartilage CC, and the percutaneous access points for performing the procedures of the present invention will be located beneath the rib cage RC, and preferably between the xiphoid X and an adjacent costal cartilage CC, preferably at the access location AL shown by a broken line.

An exemplary tool 10 for performing the methods of the present invention is illustrated in FIGS. 3, 3A, and 4A–4C. The tool comprises a shaft 12 having a distal end 14 and a proximal end 16. A handle 18 is preferably attached to the proximal end of the shaft, and the shaft will have a curved profile in its axial direction (as best seen in FIG. 4B) and a crescent-shaped cross-section, as best seen in FIG. 4C. The preferred dimensions of the shaft are set forth above.

In the illustrated embodiment, the shaft has three lumens 20, 22, and 24. A first lumen 20 is used for introducing a closure tool (which may be any of the closure tools described above), while the second and third lumens (22 and 24, respectively) are used for introducing a viewing scope and fluids, such as saline or other clear fluids for improving visualization of the region surrounding the left atrial appendage. In alternative embodiments, the first lumen 20 can still be used for a grasper, while either of the second lumen 22 and/or third lumen 24 may be used for introducing alternative closure devices, such as clip appliers, riveting devices, fusing devices, suturing devices, stapling devices, or the like. In a particular embodiment shown below, either or both of the lumens 22 and 24 may be used to advance a clip over the left atrial appendage as the appendage is being grasped by a grasper, such as the one shown in FIG. 3.

Figure 3A:
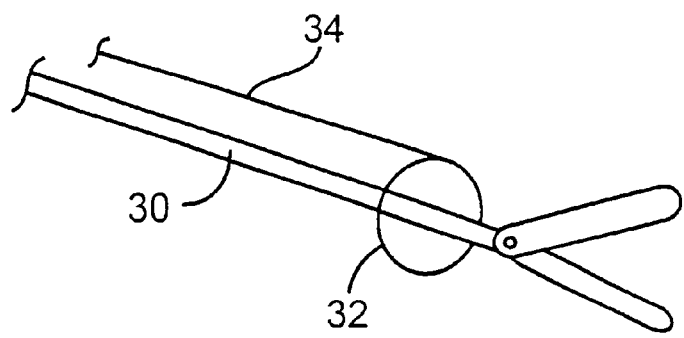
FIG. 3 is a perspective view of an exemplary closure tool useful for performing the methods of the present invention.
Figure 3:
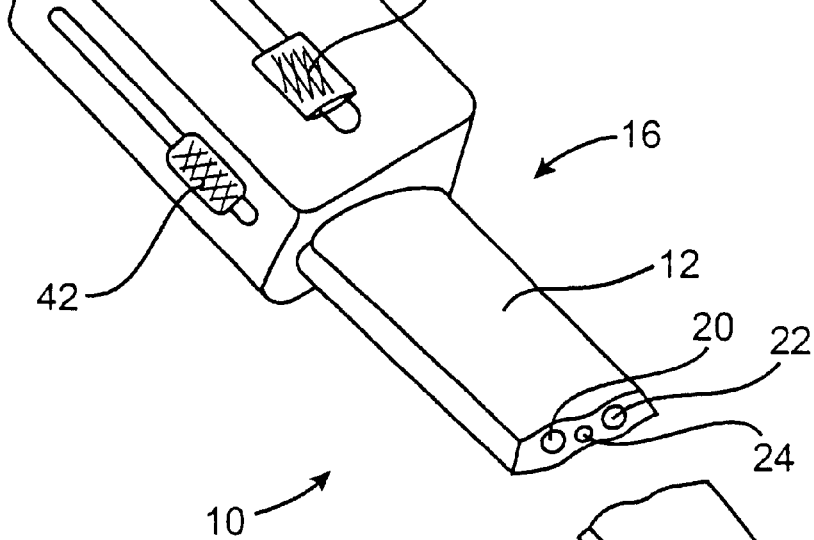
Figure 3:
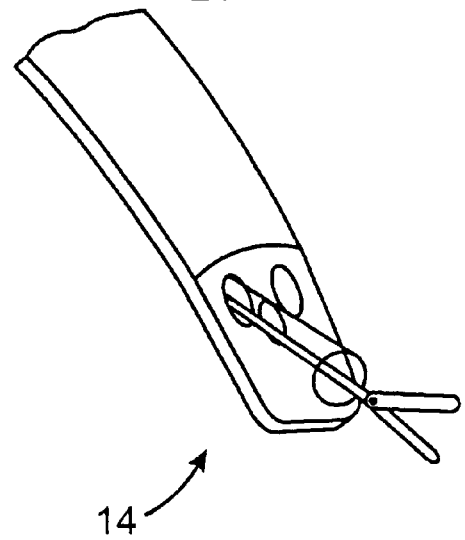

While the closure tool may have any of a wide variety of designs, the presently preferred tool is shown in FIG. 3A. The tool comprises a grasper 30 and a capture loop 32. Capture loop 32 is attached to a manipulation wire 34 which permits the loop 32 to be advanced over the forward end of the grasper to encircle and close the left atrial appendage, as will be described in more detail below. The grasping tool 32 may be manipulated using a thumb guide 40, while the capture loop 32 may be manipulated using a second thumb guide 42, both of which are located on the handle 18.

The lumens 20, 22, and 24, terminate in exit ports 50, 52, and 54, best seen in FIG. 4A. The exit ports are located proximally of the distal end 14 of the shaft 12. The shaft is generally thinned in the region between the exit ports and the distal tip, facilitating the introduction of the distal tip into the atrioventricular groove, as described in more detail below. The exit ports are located a sufficient distance behind the distal tip of the shaft so that they will be generally located adjacent to the free end of the left atrial appendage when the tip is located in the atrioventricular groove.

Figure 5:
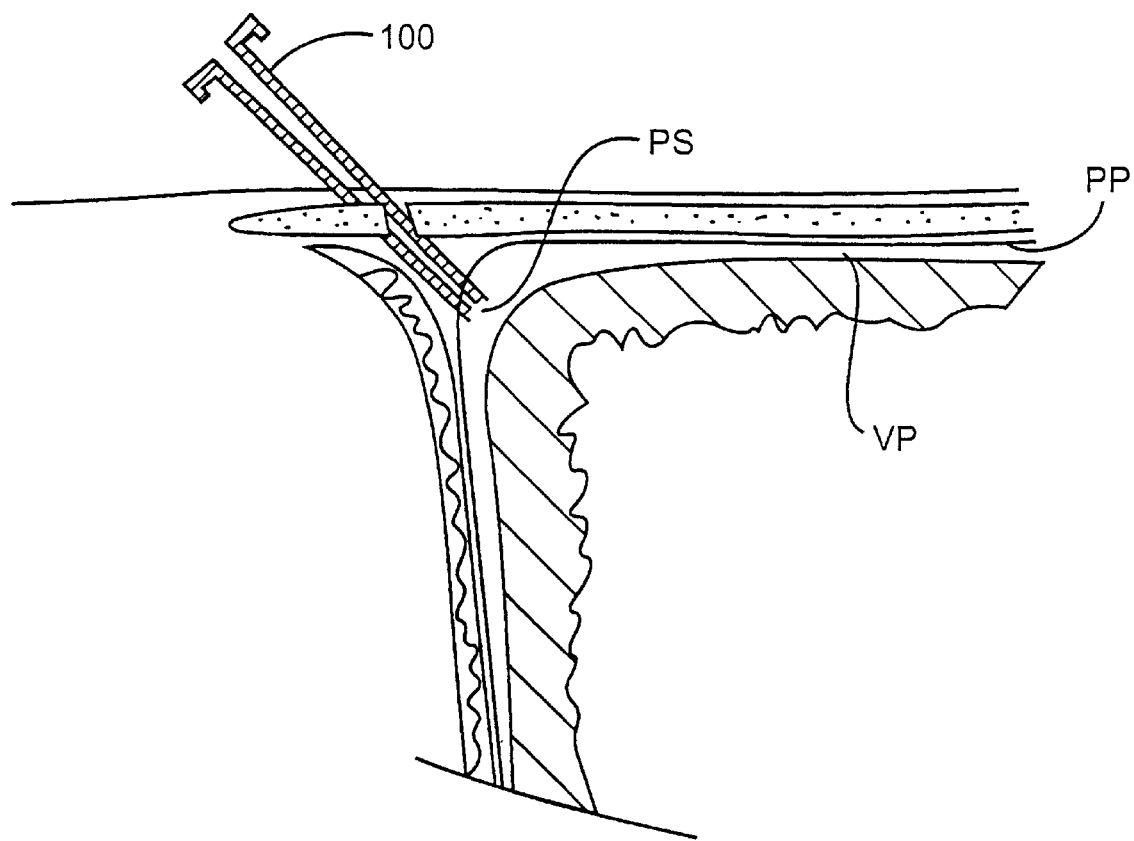
FIG. 5 illustrates an access sheath placed percutaneously into a pericardial space using a sub-xiphoid approach beneath the rib cage as is preferred in the methods of the present invention.
Figure 6A:
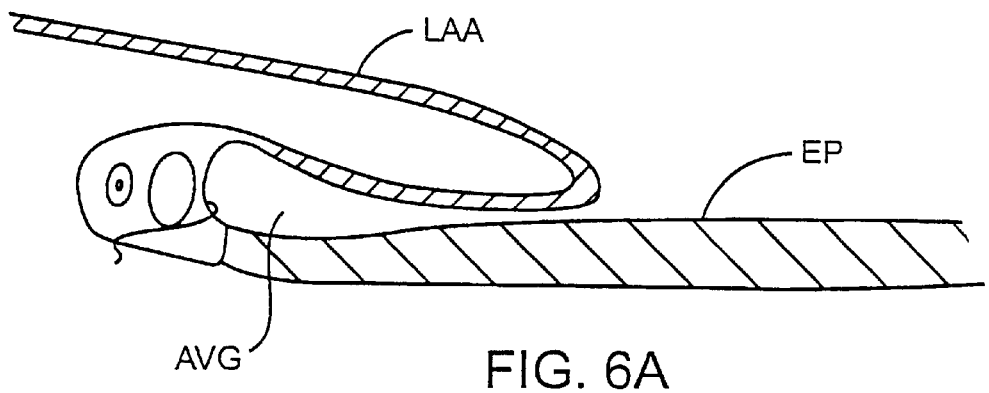
FIGS. 6A–6G illustrate use of the exemplary tool of FIG. 3 in performing the closure of a left atrial appendage according to the methods of the present invention.
Figure 6B:
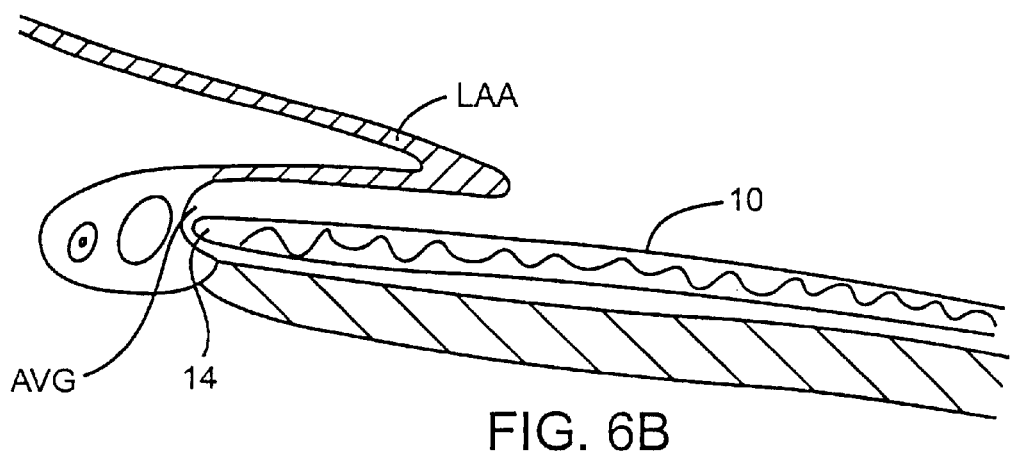
Figure 6C:
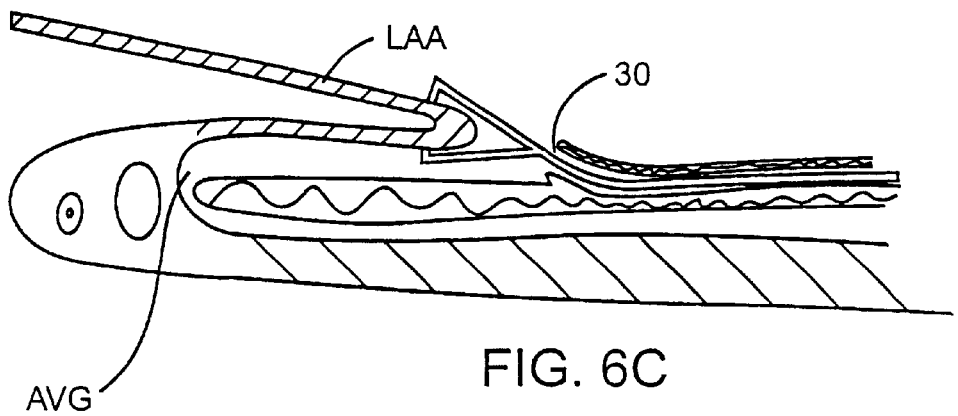
Figure 6D:
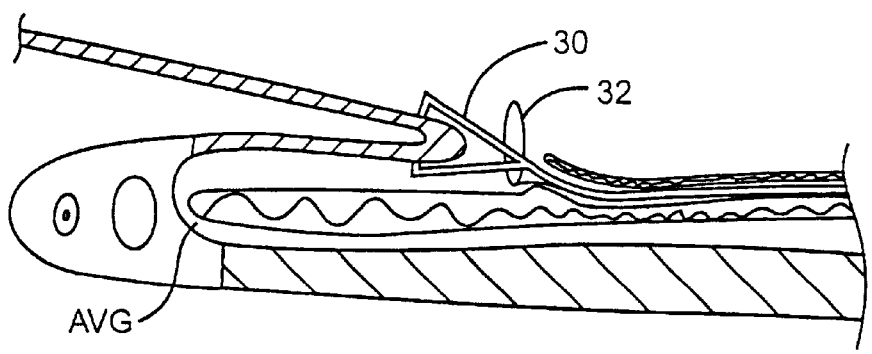
Figure 6E:
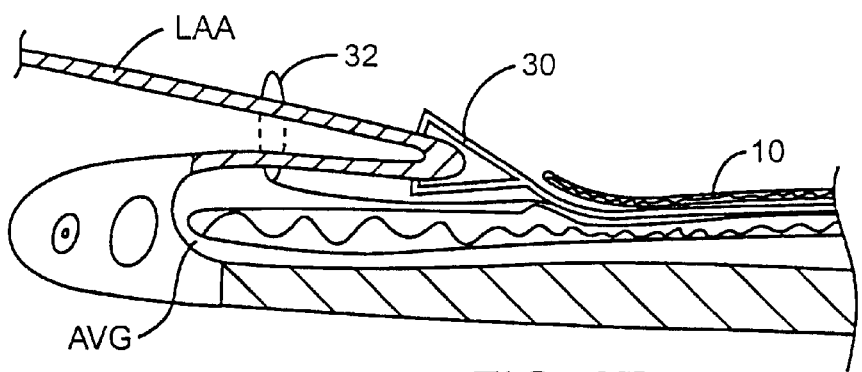
Figure 6F:
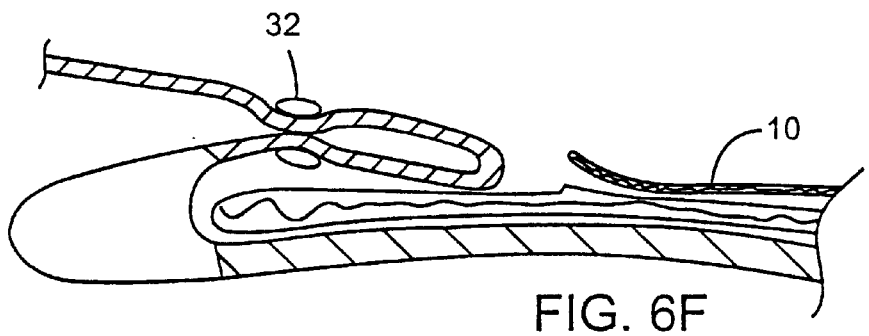
Figure 6G:
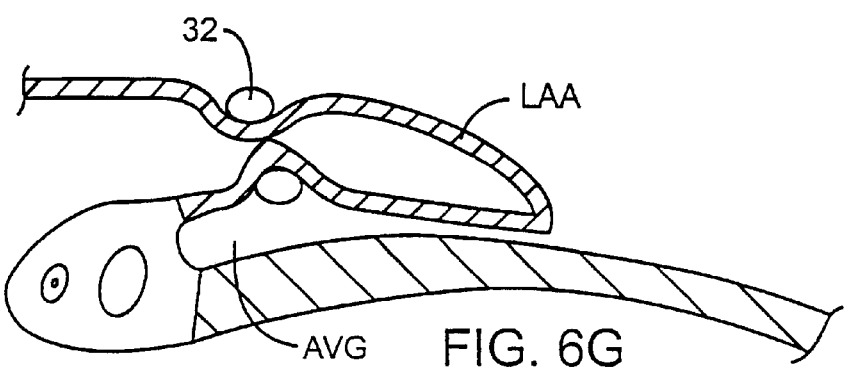

The methods of the present invention may be performed in an ambulatory surgical setting. Typically, a sedated patient is taken to a facility having fluoroscopic imaging capabilities. The area overlying the xiphoid and adjacent costal cartilage, is prepared and draped using standard techniques. A local anesthetic is then administered and a skin incision, usually about 2 cm in length made, at the area shown in FIG. 2. The percutaneous penetration passes beneath the costal cartilage, and a sheath 100 (FIG. 5) is introduced into the pericardial space PS. The pericardial space PS is then irrigated with saline, preferably with a saline-lidocaine solution to provide additional anesthesia and reduce the risk of irritating the heart. The closure device 10 is then introduced through the sheath 100 into the pericardial space and advanced over the epicardium to the atrioventricular groove AVG (as shown in FIG. 6A and FIG. 6B). The grasping tool 30 is then advanced distally from the tool 10 so that it can grasp the free end of the left atrial appendage LAA, as shown in FIG. 6C. A slight tension can be applied on the left atrial appendage LAA as the capture loop 32 is advanced over the grasper 30 (FIG. 6D), and on to the left atrial appendage LAA, as shown in FIG. 6E. The loop may then be cinched, as shown in FIG. 6F, and the tool 10 withdrawn leaving the closure loop in place, as shown in FIG. 6G. The interior of the left atrial appendage LAA is thus isolated from the interior of the left atrium so that thrombus and other emboli cannot be released into blood circulation.

Figure 6H:
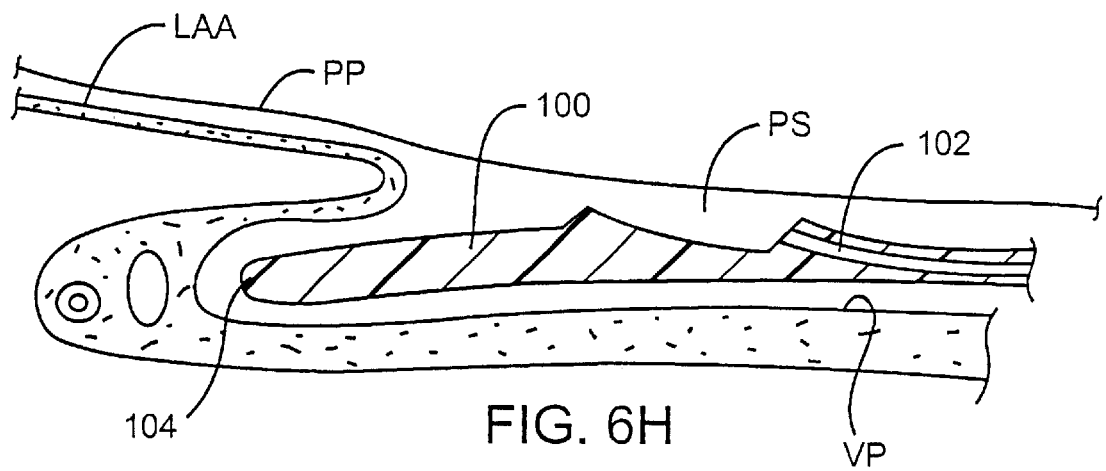
FIGS. 6K–6N illustrate an alternative protocol for use of the exemplary tool of FIG. 3 in performing the closure of a left atrial appendage according to the methods of the present invention.
FIGS. 6O and 6P illustrate alternative clip placement patterns for closing the left atrial appendage according to the methods of the present invention.
Figure 6I:
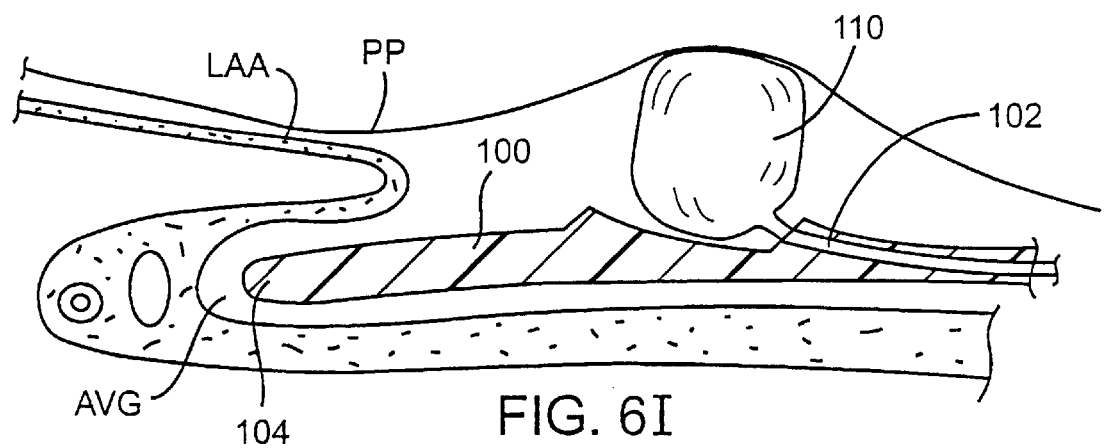
Figure 6J:
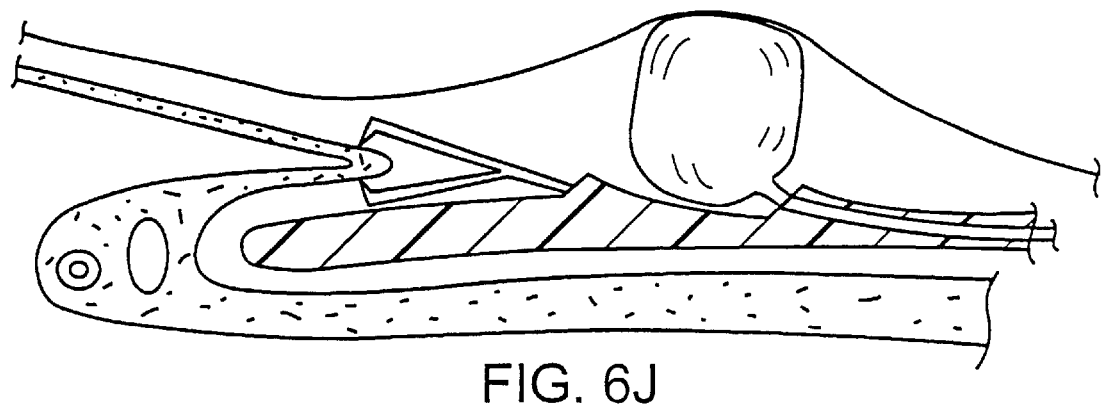
Figure 6K:
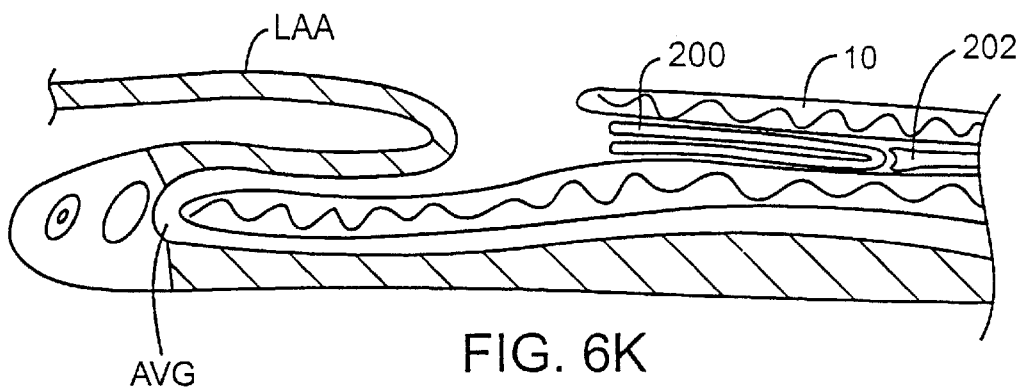

Optionally, a portion of the parietal pericardium may be further separated from the epicardial surface and the left atrial appendage prior to closing the appendage. Increasing the distance between the parietal and visceral pericardium, i.e., the pericardial space, creates a working and viewing space that facilitates subsequent manipulation and closure of the atrial appendage. As shown in FIGS. 6H–6J, a modified closure device 100 having an additional lumen 102 is introduced so that its distal end 104 enters the atrioventricular groove AVG, as described previously. A balloon expander 110 may then be introduced through the lumen 102, and the balloon expanded to raise the pericardium, as shown in FIG. 6I. The grasper 30 (or other closure instrument) may then be introduced through other lumens, as previously described. The working space created by the balloon greatly simplifies manipulation and positioning of the graspers 30 so that they can be used to capture the atrial appendage and close it as described previously. Further separating the parietal and visceral pericardia to create the working space is a particular advantage when a viewing scope is introduced to the working area to facilitate manipulation of the grasper 30 and any other tools which may be used.

Figure 6L:
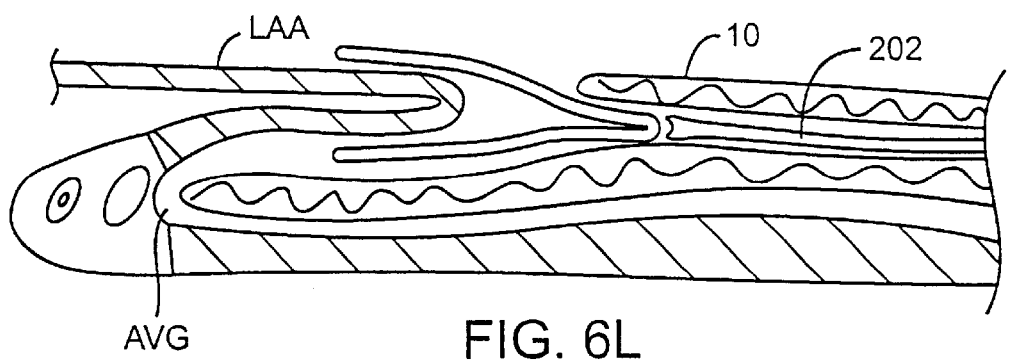
Figure 6M:
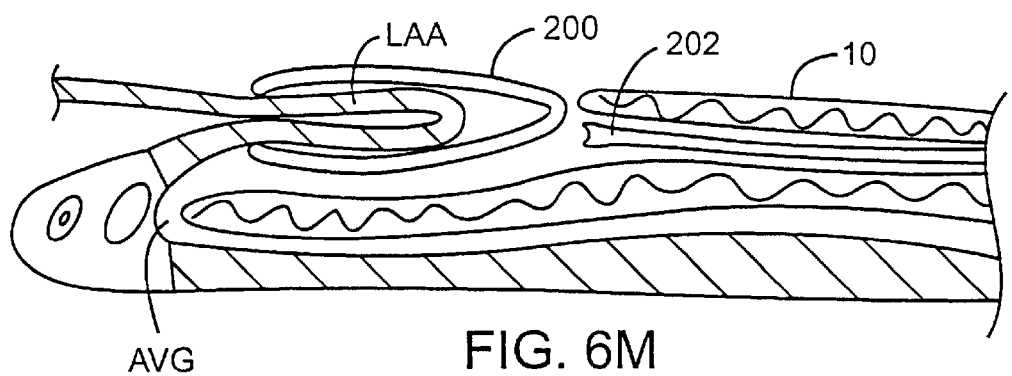
Figure 6N:
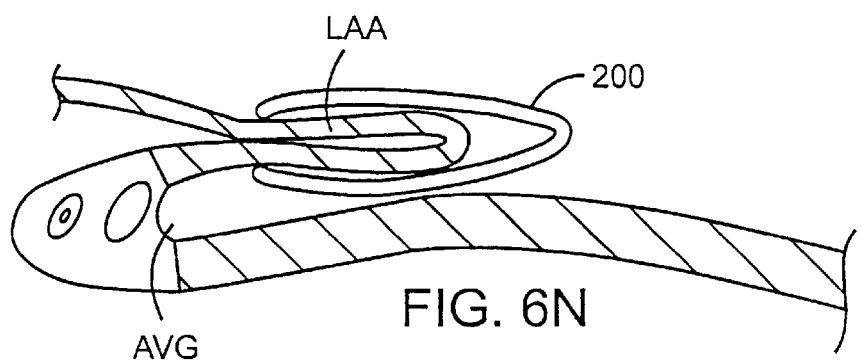
Figure 6O:
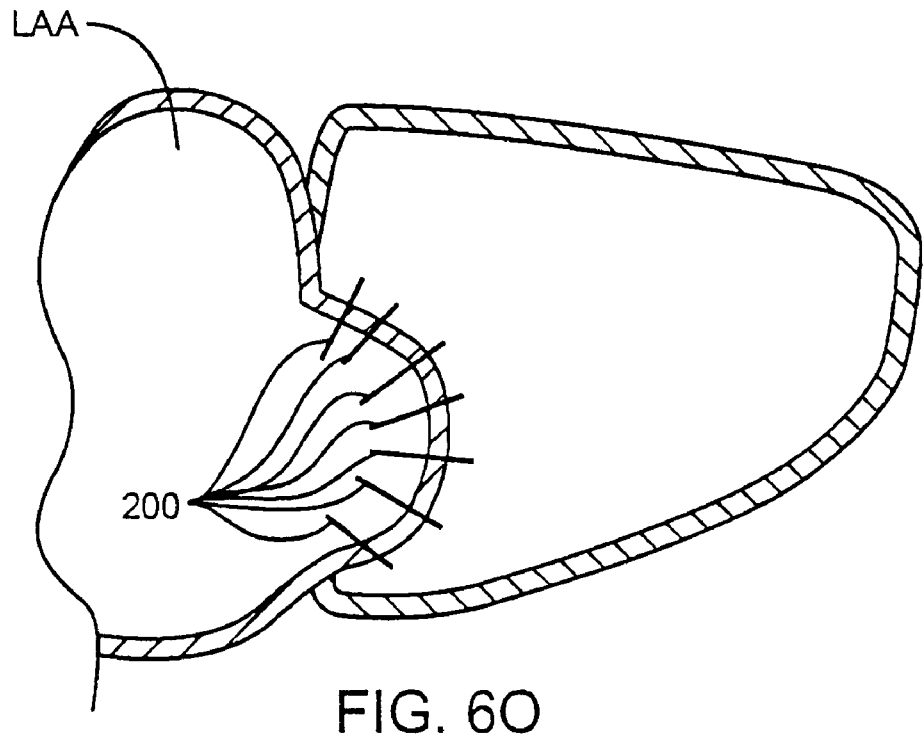
Figure 6P:
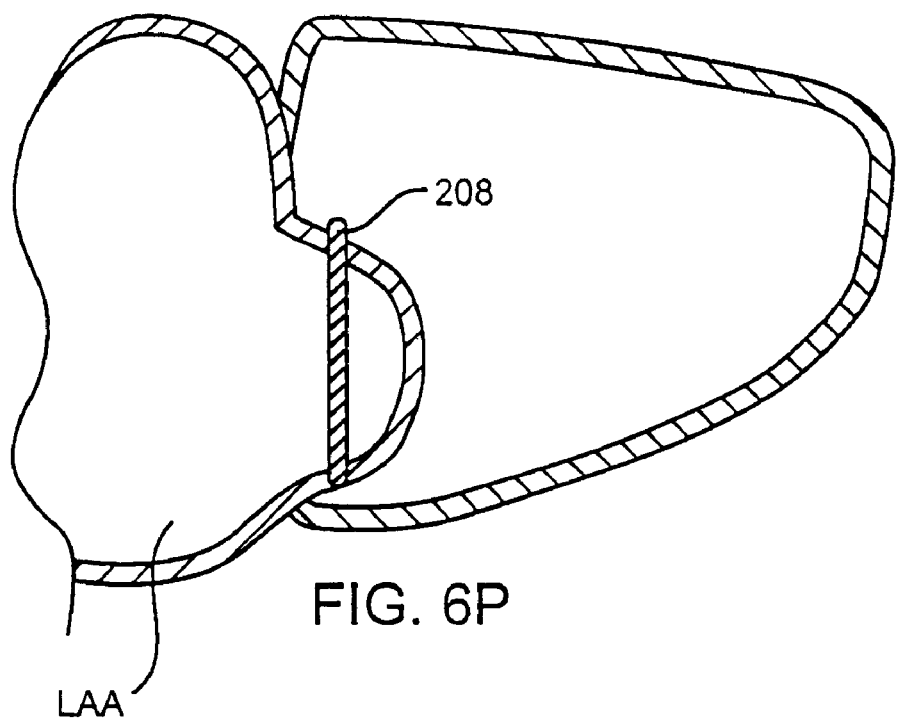

Referring now to FIGS. 6K–6N, the closure tool 10 is illustrated in a method for introducing a clip 200 in accordance with the principles of the present invention. The closure tool 10 is introduced to the left atrial appendage LAA as described in above in connection with FIGS. 6A and 6B. Once in place, the clip 200 may be introduced through any of the available lumens in the device, typically using a pusher 202. The clip 200 will be configured so that it opens as it emerges from the closure tool 10 and can be advanced over the free distal end of the left atrial appendage LAA, as shown in FIG. 6L. The clip 200 may then be closed over the appendage, as shown in FIG. 6N. The clip 200 may be self-closing or may require a mechanical or heat-actuated closure mechanism. Once in place, as shown in FIG. 6N, the closure tool 10 can be removed. Frequently, it will be desirable to introduce multiple clips 200, as shown in FIG. 6O. Alternatively, a larger clip 208 can be introduced transversely over the left atrial appendage LAA, as shown in FIG. 6P.

Referring now to FIGS. 7A–7C, an exemplary clip 300 for use in the methods of the present invention will be described. The clip 300 has a generally U-shaped profile, as best seen in FIG. 7A, optionally having a serpentine or zig-zag profile on at least one of the legs of the clip. As illustrated, a series of peaks and valleys 302 is provided on an "upper" leg of the clip. The clip 300 further includes a hinge region 304 which has a narrowed width to facilitate introduction through a introducer catheter 400, as shown in FIG. 8. Introducer catheter 400 has a I-shaped lumen 402 which receives the clip 300 so that the upper leg and lower leg of the clip are held in an open configuration in upper and lower tracks of the lumen, as described below in connection with FIGS. 9A–9C. Optionally, the catheter 400 may include a radiopaque marker 404 to permit orientation under fluoroscopic imaging (so the position can confirm that the clip is in the proper vertical orientation when being placed). A pusher 408 is provided having a I-shaped distal end 410 which is received in the I-shaped lumen 402 in order to advance and eject the clip from the catheter.

Figure 9A:
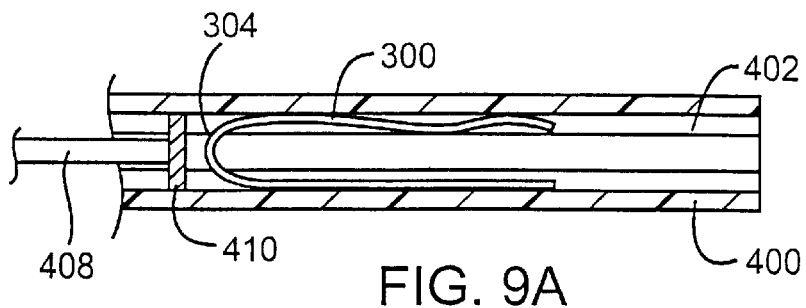
FIGS. 9A–9C are cross-sectional views of the insertion tool of FIG. 8 used in placing the clip of FIGS. 7A–7C over a left atrial appendage according to the methods of the present invention.
Figure 9B:
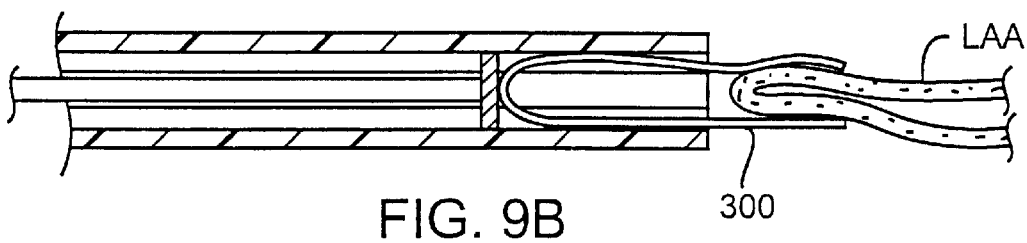
Figure 9C:
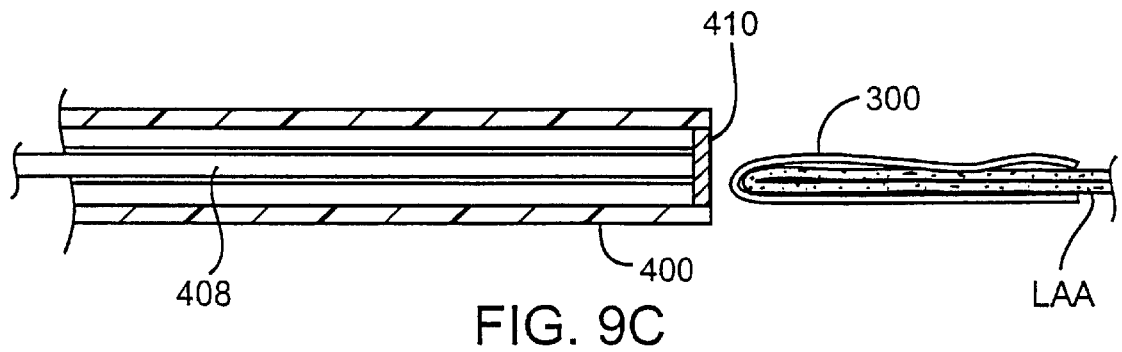

Referring now to FIGS. 9A–9C, the clip 300 is held in the lumen 402 of catheter 400 with the legs of the clip held open. A pusher 408 can be advanced so that end 410 engages the hinge region 304 of the clip, allowing it to be advanced out of the distal end of the catheter, as shown in FIG. 9B. As the clip 300 emerges, it remains in an open configuration so that it can be advanced over a free distal end of the left atrial appendage LAA, as shown in FIG. 9B. Once the clip 300 is fully advanced and released from the catheter 400, as shown in FIG. 9C, the clip will close over the left atrial appendage LAA to hold the appendage closed in accordance with the principles of the present invention.

Figure 10:
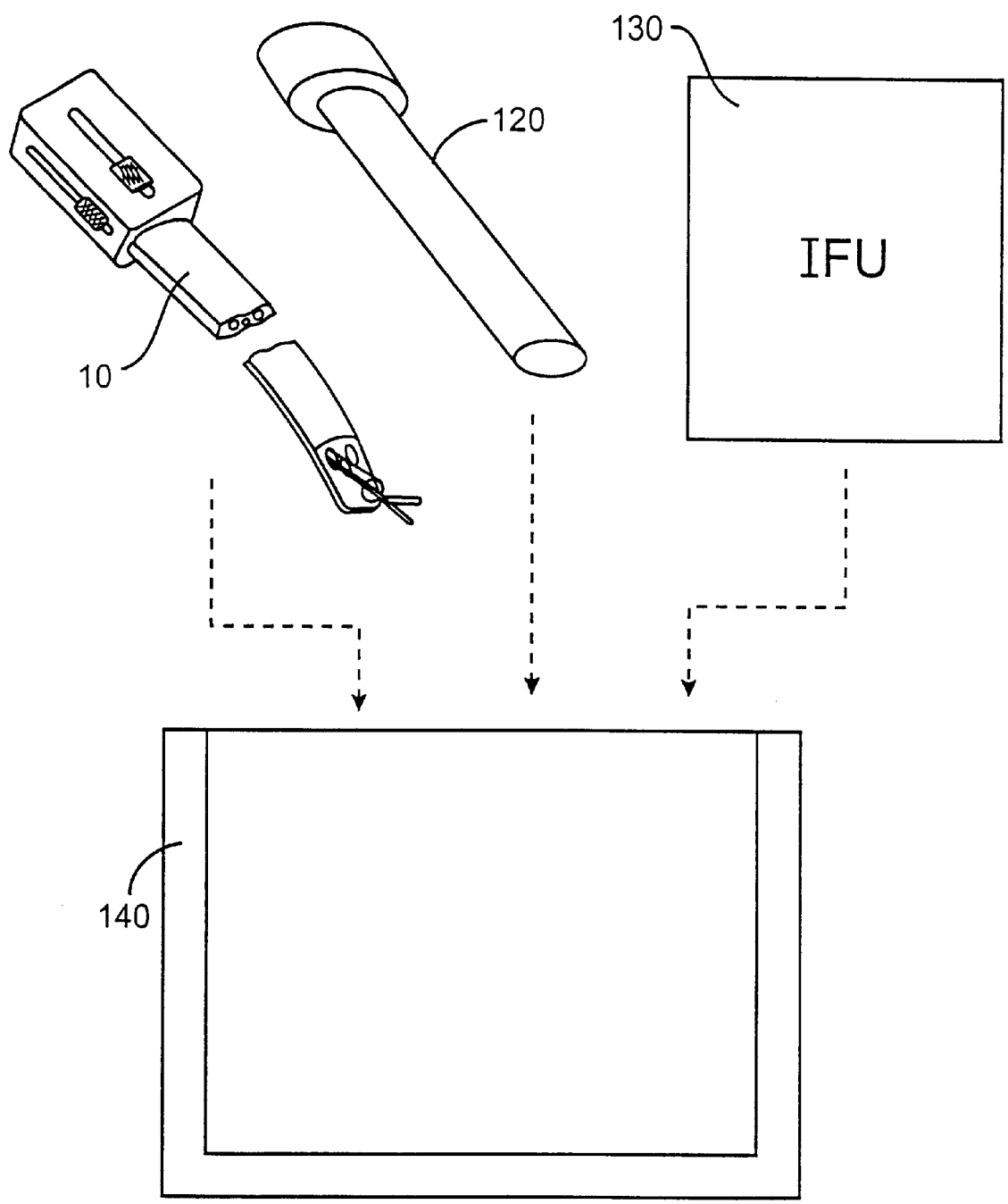
FIG. 10 illustrates an exemplary kit including a closure device and optional components according to the present invention.

Referring now to FIG. 10, kits according to the present invention comprise a closure tool, such as closure tool 10 described above. Optionally, the kits may comprise an access sheath 120 and will include instructions for use IFU setting forth any of the methods described above. Usually, all components of the kit will be packaged together in an enclosure 140, such as a pouch, tray, box, tube, or other conventional surgical package capable of maintaining the components in a sterile condition. It will be appreciated that any kit containing instructions for use setting forth the methods of the present invention will be part of the present invention. Whether or not the kits include a closure device which is similar to FIG. 10 is not necessary.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for closing a left atrial appendage of a patient's heart, said method comprising:

making an incision between a costal cartilage and a xiphoid of the patient;

placing an access sheath through the incision into a pericardial space;

positioning a closure instrument through the access sheath into the pericardial space beneath the rib cage, over an epicardial surface, and adjacent to the left atrial appendage; and closing the left atrial appendage using the closure instrument.

2. A method as in claim 1, wherein positioning further comprises advancing a distal end of the closure instrument through the sheath, into the pericardial space, and over an epicardial surface to an atrioventricular groove of the heart.

3. A method as in claim 2, wherein closing comprises looping, suturing, stapling, clipping, riveting, clamping, or fusing the left atrial appendage at a neck region thereof.

4. A method as in claim 3, wherein closing further comprises grasping the left atrial appendage prior to closing the neck region thereof.

5. A method as in claim 1, wherein the method is performed while the patient's heart is beating.

6. A method as in claim 5, wherein the method is performed while both lungs of the patient remain inflated.

7. A method as in claim 6, wherein the method is performed while the patient is under a local anesthetic.

8. An improved method for closing a left atrial appendage of a heart, said method being of the type wherein a closure element is placed over an exterior of the appendage while the patient's chest remains closed, wherein the improvement comprises advancing the closure element from beneath the rib cage over an epicardial surface to the exterior of the left atrial appendage prior to placing the closure element over the left atrial appendage.

9. A method as in claim 1, further comprising separating the parietal pericardium from the visceral pericardium near left atrial appendage prior to closing the left atrial appendage to create a space over the atrial appendage.

10. A method as in claim 9, further comprising viewing the atrial appendage through the space.

11. A method for closing a left atrial appendage of a patient's heart, said method comprising:

positioning a closure instrument through a percutaneous passage into a pericardial space beneath the rib cage, over an epicardial surface, and adjacent to the left atrial appendage, without passing through the pleural space; and closing the left atrial appendage using the closure instrument.

12. A method as in claim 11, wherein positioning comprises making an incision between a costal cartilage and a xiphoid of the patient and placing an access sheath through the incision into the pericardial space.

13. A method as in claim 12, wherein positioning further comprises advancing a distal end of the closure instrument through the sheath, into the pericardial space, and over an epicardial surface to an atrioventricular groove of the heart.

14. A method as in claim 13, wherein closing comprises looping, suturing, stapling, clipping, riveting, clamping, or fusing the left atrial appendage at a neck region thereof.

15. A method as in claim 14, wherein closing further comprises grasping the left atrial appendage prior to closing the neck region thereof.

16. A method as in claim 11, wherein the method is performed while the patient's heart is beating.

17. A method as in claim 16, wherein the method is performed while both lungs of the patient remain inflated.

18. A method as in claim 17, wherein the method is performed while the patient is under a local anesthetic.

19. A method as in claim 11, further comprising separating the parietal pericardium from the visceral pericardium near the left atrial appendage prior to closing the left atrial appendage to create a space over the atrial appendage.

20. A method as in claim 19, further comprising viewing the atrial appendage through the space.

21. A method for closing a left atrial appendage of a patient's heart, said method comprising:

positioning a closure instrument through a percutaneous passage into a pericardial space beneath the rib cage, over an epicardial surface, and adjacent to the left atrial appendage, while both lungs of the patient remain inflated; and closing the left atrial appendage using the closure instrument.

22. A method as in claim 21, wherein positioning comprises making an incision between a costal cartilage and a xiphoid of the patient and placing an access sheath through the incision into the pericardial space.

23. A method as in claim 22, wherein positioning further comprises advancing a distal end of the closure instrument through the sheath, into the pericardial space, and over an epicardial surface to an atrioventricular groove of the heart.

24. A method as in claim 23, wherein closing comprises looping, suturing, stapling, clipping, riveting, clamping, or fusing the left atrial appendage at a neck region thereof.

25. A method as in claim 24, wherein closing further comprises grasping the left atrial appendage prior to closing the neck region thereof.

26. A method as in claim 21, wherein the method is performed while the patient's heart is beating.

27. A method as in claim 21, wherein the method is performed while the patient is under a local anesthetic.

28. A method as in claim 21, further comprising separating the parietal pericardium from the visceral pericardium near the left atrial appendage prior to closing the left atrial appendage to create a space over the atrial appendage.

29. A method as in claim 28, further comprising viewing the atrial appendage through the space.

30. A method for closing a left atrial appendage of a patient's heart, said method comprising:

inserting a closure instrument through a percutaneous passage;

introducing the closure instrument into a pericardial space by passing the closure instrument beneath the rib cage, over an epicardial surface, and adjacent to the left atrial appendage, without passing through the pleural space; and closing the left atrial appendage using the closure instrument.

31. A method as in claim 30, wherein inserting comprises making an incision between a costal cartilage and a xiphoid of the patient and placing an access sheath through the incision into the pericardial space.

32. A method as in claim 31, wherein introducing further comprises advancing a distal end of the closure instrument through the sheath, into the pericardial space, and over an epicardial surface to an atrioventricular groove of the heart.

33. A method as in claim 32, wherein closing comprises looping, suturing, stapling, clipping, riveting, clamping, or fusing the left atrial appendage at a neck region thereof.

34. A method as in claim 33, wherein closing further comprises grasping the left atrial appendage prior to closing the neck region thereof.

35. A method as in claim 30, wherein the method is performed while the patient's heart is beating.

36. A method as in claim 35, wherein the method is performed while both lungs of the patient remain inflated.

37. A method as in claim 36, wherein the method is performed while the patient is under a local anesthetic.

38. A method as in claim 30, further comprising separating the parietal pericardium from the visceral pericardium near the left atrial appendage prior to closing the left atrial appendage to create a space over the atrial appendage.

39. A method as in claim 38, further comprising viewing the atrial appendage through the space.

* * * * *

UNITED STATES PATENT AND TRADEMARK OFFICE
CERTIFICATE OF CORRECTION

PATENT NO.   : 6,488,689 B1                                                      Page 1 of 1
DATED        : December 3, 2002
INVENTOR(S)  : Aaron V. Kaplan and Jordan T. Bajor It is certified that error appears in the above-identified patent and that said Letters Patent is hereby corrected as shown below:

<u>Column 5,</u>
After line 11, please insert the following text:
-- FIGS. 6H-6J illustrate a modified closure device for introduction of a balloon expander. --

Signed and Sealed this

Third Day of June, 2003

JAMES E. ROGAN
*Director of the United States Patent and Trademark Office*